United States Patent [19]

Baumann

[11] Patent Number: 5,290,311
[45] Date of Patent: Mar. 1, 1994

[54] FEMORAL HEAD SHAFT PROSTHESIS

[76] Inventor: Friedrich Baumann, Am Kirchberg 2, 8858 Neuberg/Donau, Fed. Rep. of Germany

[21] Appl. No.: 20,903

[22] Filed: Feb. 22, 1993

Related U.S. Application Data

[63] Continuation of Ser. No. 816,114, Jan. 2, 1992, abandoned.

[30] Foreign Application Priority Data

Jan. 21, 1990 [DE] Fed. Rep. of Germany ....... 4101587

[51] Int. Cl.$^5$ ................................................. A61F 1/24
[52] U.S. Cl. ......................................... 623/23; 623/18
[58] Field of Search ......................... 623/22, 16, 23, 18

[56] References Cited

U.S. PATENT DOCUMENTS

| | | | |
|---|---|---|---|
| 4,314,381 | 2/1982 | Koeneman | 623/22 |
| 4,430,761 | 2/1984 | Niederer et al. | 623/18 |
| 4,535,487 | 8/1985 | Esper et al. | 623/18 X |
| 4,536,894 | 8/1985 | Galante et al. | 623/18 X |
| 4,563,778 | 1/1986 | Roche et al. | 623/22 |
| 4,566,138 | 1/1986 | Lewis et al. | 623/22 |
| 4,636,219 | 1/1987 | Pratt et al. | 623/22 |
| 4,801,300 | 1/1989 | Kurze et al. | 623/22 |
| 4,827,919 | 5/1989 | Barbarito et al. | 128/924 |
| 4,892,551 | 1/1990 | Haber | 623/18 X |
| 5,116,380 | 5/1992 | Hewka et al. | 623/18 X |

FOREIGN PATENT DOCUMENTS

| | | | |
|---|---|---|---|
| 3740438 | 6/1989 | Fed. Rep. of Germany | 623/18 |
| 3806870 | 9/1989 | Fed. Rep. of Germany | 623/18 |
| 8800031 | 1/1988 | World Int. Prop. O. | 623/18 |

Primary Examiner—David Isabella
Assistant Examiner—Debra S. Brittingham
Attorney, Agent, or Firm—Cort Flint; Henry S. Jaudon

[57] ABSTRACT

A femoral head shaft prothesis is disclosed with an oblong shaft portion (2, 3) which can be implanted into a marrow cavity (not shown) of an upper thigh bone and can be attached therein by means of a cement layer. According to the invention raised areas in the form of nub rows (17, 18, 19, 21) with small surfaces by comparison to the size of the circumference of the shaft portion (2, 3) are formed at a small number of appropriate locations on said circumference of said shaft portion to serve as spacers in relation to the inner wall of the marrow cavity. The lower shaft portion (2) is formed to be cylindrical and is intended to be inserted into a cylindrically drilled marrow cavity of the femoral neck stump. In this manner a uniform cement layer thickness with only minimal interruptions is achieved, ensuring primary and long-term stability.

18 Claims, 2 Drawing Sheets

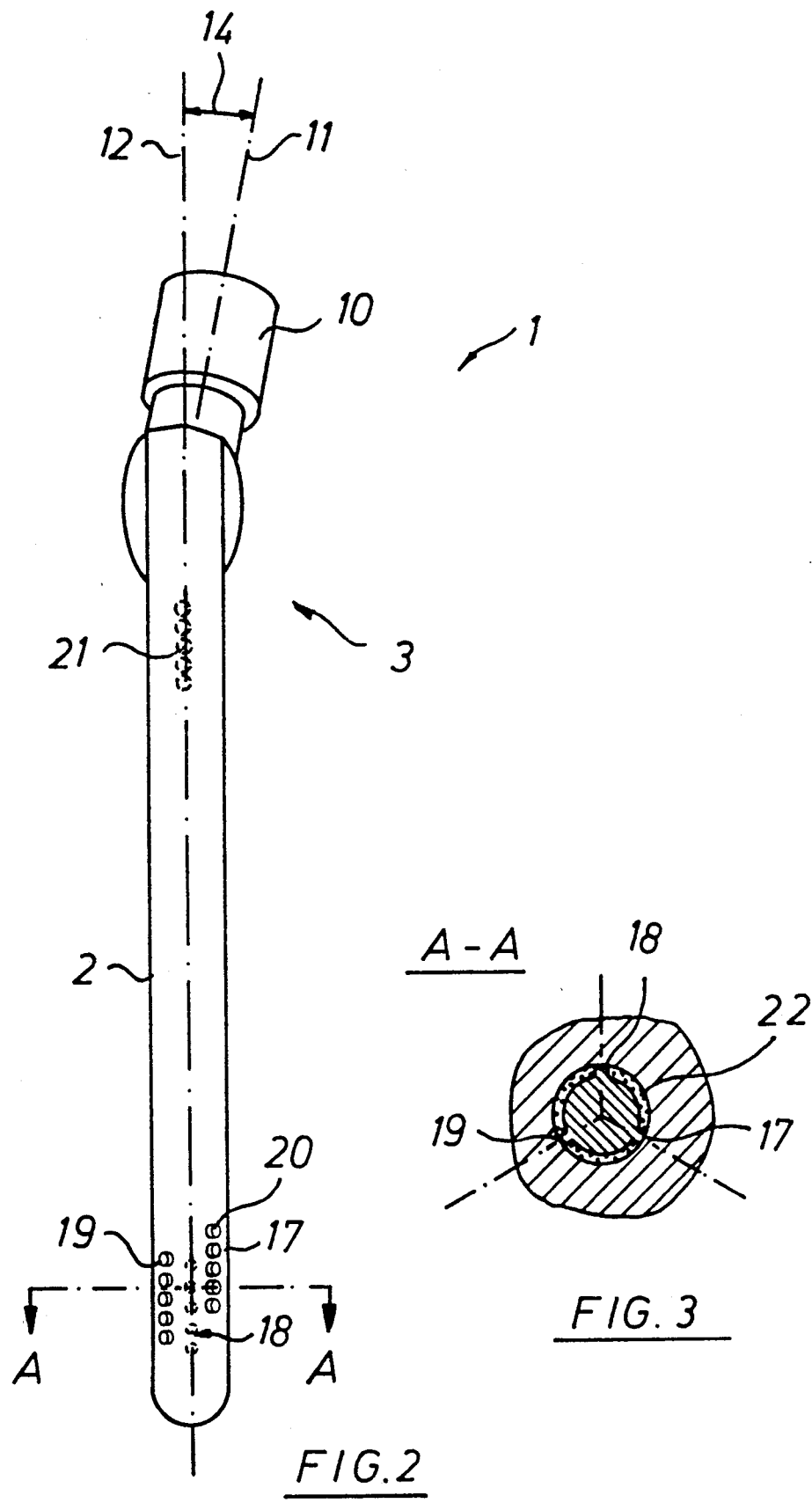

FEMORAL HEAD SHAFT PROSTHESIS

This is a continuation of copending application Ser. No. 07/816,114 filed on Jan. 2, 1991, now abandoned.

BACKGROUND OF THE INVENTION

The invention pertains to a femoral head shaft prosthesis and, in particular, to a femoral head shaft prosthesis with a shaft portion which can be implanted into the marrow cavity of the femoral neck stump and can be attached in the marrow cavity by a cement layer surrounding the shaft portion.

A femoral head shaft prosthesis acts in a known manner together with a pin which can be screwed into the pelvic bone and which is threaded on the outside on a titanium outer dome. The outer dome is preferably conical in order to ensure increased support in addition to the contact with the threads. The inner cup of the pan is made of polyethylene which yields the best tribological values especially in combination with a ceramic finish of the femoral head.

Problems have arisen in the past, especially with respect to the primary stability and the long-term stability of the shaft portion in the marrow cavity of the upper thigh. Basically, two types of attachment are known. In a first process which used to be carried out regularly in the past, the shaft portion is attached by means of a cement combination in the marrow cavity of the upper thigh. The invention relates to a femoral head shaft prosthesis for this type of attachment which is still used today when it is necessary to put loads on the femoral head early, e.g. with older people.

The second process consists in cement-free implantation of a self-healing femoral head shaft prosthesis. A known method for this consists in coating the surface with hydroxyl apatite which induces the formation of new bone and promotes the incorporation of the prosthesis shaft through healing. Difficulties occur due to the fact that the marrow cavity in the femoral neck is physiologically different in each person, bends forward and to the outside to some extent and also varies in its cross-section. For this reason the known prosthesis shafts have been made in different shapes, and especially elliptical cross-sections and so-called physiological curves were produced.

With an implantation without cement all of these models have in common that the prosthesis shafts make contact only at points or over very small surfaces in the marrow cavity of the femoral neck so that incorporation through healing is delayed and impeded due to the initially unstable seating of the prothesis shaft.

To bring about an improvement in this matter, the implantation without cement of a femoral head shaft prosthesis has already become known (EP 0,359,097 A1) in which the lower portion of the shaft is cylindrical and can be implanted into a marrow cavity which has been drilled cylindrically to an equal diameter. Large contact surfaces with great primary stability and improved bone incorporation is thus achieved. The main problems with a cemented embodiment of a femoral head shaft prosthesis are basically different ones. To attach the prothesis shaft the latter is introduced with its relatively smooth surfaces into the marrow cavity which has been prepared with cement. A known embodiment (DE 32 47 726 A1) has a conical shaft tapering conically downward. The shaft bears here with portions of its circumference directly upon the inner wall of the marrow cavity so that direct contact is effected therein without intermediate cement layer. Due to the lack of a cement layer where direct contact occurs there is no bonding, so that the required strong fixing is reduced. A particular disadvantage is however especially due to the fact that the gap for the cement layer next to the points of direct contact first widens gradually so that the cement layer is very thin there and its layer thickness only increases at a further distance from the point of contact. This very thin cement layer in immediate proximity of the direct points of contact tends to come loose and to crumble because of its low internal stability. As a result the connection and the firm support are further reduced in the area adjoining the points of contact. Furthermore such detached cement particles have a toxic and destructive effect on the surrounding bone.

In order to achieve an improvement with respect to uniform cement layer thicknesses a method is already known by which a plastic star is pushed into the marrow cavity until it is in a position on which the underside of the prosthesis shaft will come to rest and by which the lower end of the prosthesis shaft is centered in the marrow cavity in this plastic star. For this purpose the prosthesis shaft is perforated and is set into the marrow cavity by means of a guide rod connected to the plastic star and passing through this perforation. Following the implantation the guide rod is removed. This process is obviously complicated and expensive, and despite the plastic star it cannot be ensured that the lower portion of the prosthesis shaft is seated securely and is centered in the receiving portion of the plastic star during the curing period of the cement. Also, the plastic star is a foreign body that remains disadvantageously permanently in the stump of the femoral neck. Ribbing and profiling of shaft surfaces are also known methods.

For an implantation without cement, relatively closely adjoining raised areas with small surfaces over the entire shaft surface are known and are intended to improve the anchoring of the prosthesis shaft (CH PS 675 826; DE-OS 32 16 539; DE-OS 34 15 934 and DE-GM 81 24 912). Such a surface structure with a plurality of relatively closely adjoining raised areas can provide advantages for the anchoring with an implantation without cement. When a prosthesis shaft is cemented in, such a surface structure is not suitable because the area of the cement layer would be constantly interrupted by many thinner areas and transitions so that the disadvantages described earlier in this context would occur at many locations.

Furthermore the structuring of the shaft surface by means of longitudinal grooves intended to achieve an improvement in cement bond between marrow cavity and shaft surface is also known (DE GM 88 11 758). These longitudinal grooves are however cut relatively deeply into the surface so that wide variations in the cement layer thickness are produced at the passage points between grooves and circumferences with a negative effect on stability.

It is the object of the instant invention to further develop a femoral head shaft prosthesis of this type so that improved primary and long-term stability can be achieved.

SUMMARY OF THE INVENTION

The above objectives are accomplished according to the present invention by providing a femoral head shaft prosthesis having a lower shaft portion which is cylindrical. Towards the bottom of the lower portion of the shaft raised areas or nubs which constitute spacers are provided at the circumference. They center the lower end of the lower portion of the shaft in a marrow cavity of the femoral neck stump which is a receiving cavity and is drilled cylindrically to the diameter of the outer diameter of the lower shaft portion plus the projecting spacers. The upper shaft is made on one side in form of a straight prolongation of the cylindrical lower shaft. The medial side is widened in the area of the upper shaft with a concave arc. At this location at least one raised area constituting an upper spacer for contact with the corticalis in the marrow cavity is located. Due to this arrangement of the spacers, a uniform gap and thereby a uniform thickness of cement layer with only few interruptions at the few raised spacers is created between the receiving cavity and the shaft, ensuring great primary and long-term stability.

The cement breaks below certain layer thicknesses and in areas of layer thickness differences. When cement breaks, known bone damage and bone dissolution occur due to the toxicity of the broken particles, and this has been a significant cause for frequent loosening of the shaft. The instant invention solves this problem in that a uniform cement thickness is created over the entire length of the shaft. Due to the cylindrical configuration in combination with a cylindrical preparation of the marrow cavity it suffices if only a small number of spacers are provided at the lower shaft end for centering. In the upper area, one spacer to be applied against the corticalis medial of the femoral neck stump suffices. Because of the small number of small spacers at a great distance from each other, the cement layer is interrupted only at few locations, and especially not over the entire extension of the length and the circumference.

In a preferred embodiment, the spacers are made in form of narrow rows of nubs that are relatively short by comparison to the length of the shaft, extending in the longitudinal sense of the shaft portion. Intervals are provided between the nubs. To compensate for possible diameter tolerances after cylindrical preparation of the receiving cavity and to ensure secure centering on the central axis of the cylinder, nub rows with a certain longitudinal extension are used. In order to interrupt the cement layer as little as possible by this longitudinal extension of the nub rows, intervals are provided between the nubs to allow the cement layer to pass through.

Three lower spacers or rows of nubs are provided at the circumference of the lower shaft. For the purpose of centering, three such spacers are sufficient and would then be placed advantageously far apart at an angular distance of 120° from each other and would not interrupt the cement layer over wide areas of the circumference.

The spacers or nub rows are offset against each other in shaft length or in their height. Thereby as little as possible circumferential interruption of the cement layer is advantageously achieved due to the height offset.

The height or the distance which the spacers or nubs or their length of extension from the circumference external laterally away from the shaft is preferably selected between a required minimum thickness of the cement layer of approx. 1.5 mm and approx. 3.5 mm.

In order to further increase stability, the shaft surface may be roughened, with a preferred pore depth of 0.2 to 0.6 mm. Preferably the marrow cavity is also provided with grooves in form of helicoidal grooves or longitudinal grooves on its inside. These grooves can be made in the marrow cavity with a specially formed drill. The roughing up of the shaft surface can be achieved by sand blasting. Thanks to the rough structure of the surface, improved cement bonding and thereby increased primary and long-term stability is achieved.

In one embodiment in which certain characteristics are already known, the upper shaft portion is formed on one side as a straight prolongation of the cylindrical lower portion of the shaft. The opposite medial side widens in a concave arc, preferably with a tangential angle of inclination of 10° against the long side. As a result an approximately triangular surface is produced with a thickness being that of the diameter of the cylindrical lower portion of the shaft, and defined by a vertical limit, a horizontal limit and the concave arc-shaped limit. The femoral head portion, preferably in form of a cone with a cone axis at a 40° angle from the longitudinal axis follows at the point where the horizontal and the arc-shaped limits meet.

The placing of a collar of known art may be placed below the femoral head portion, preferably at a 50° angle from the longitudinal axis, to be applied against the resection plane of the femoral neck.

DESCRIPTION OF THE DRAWINGS

The construction designed to carry out the invention will hereinafter be described, together with other features thereof.

The invention will be more readily understood from a reading of the following specification and by reference to the accompanying drawings forming a portion thereof, wherein an example of the invention is shown and wherein:

FIG. 2 is a side elevation view rotated by 90° of the femoral head prosthesis according to FIG. 1; and FIG. 3 is a cross-section along line A—A of FIG. 2 of a femoral head shaft prosthesis cemented into the marrow cavity according to the invention.

DESCRIPTION OF A PREFERRED EMBODIMENT

Figure 1:
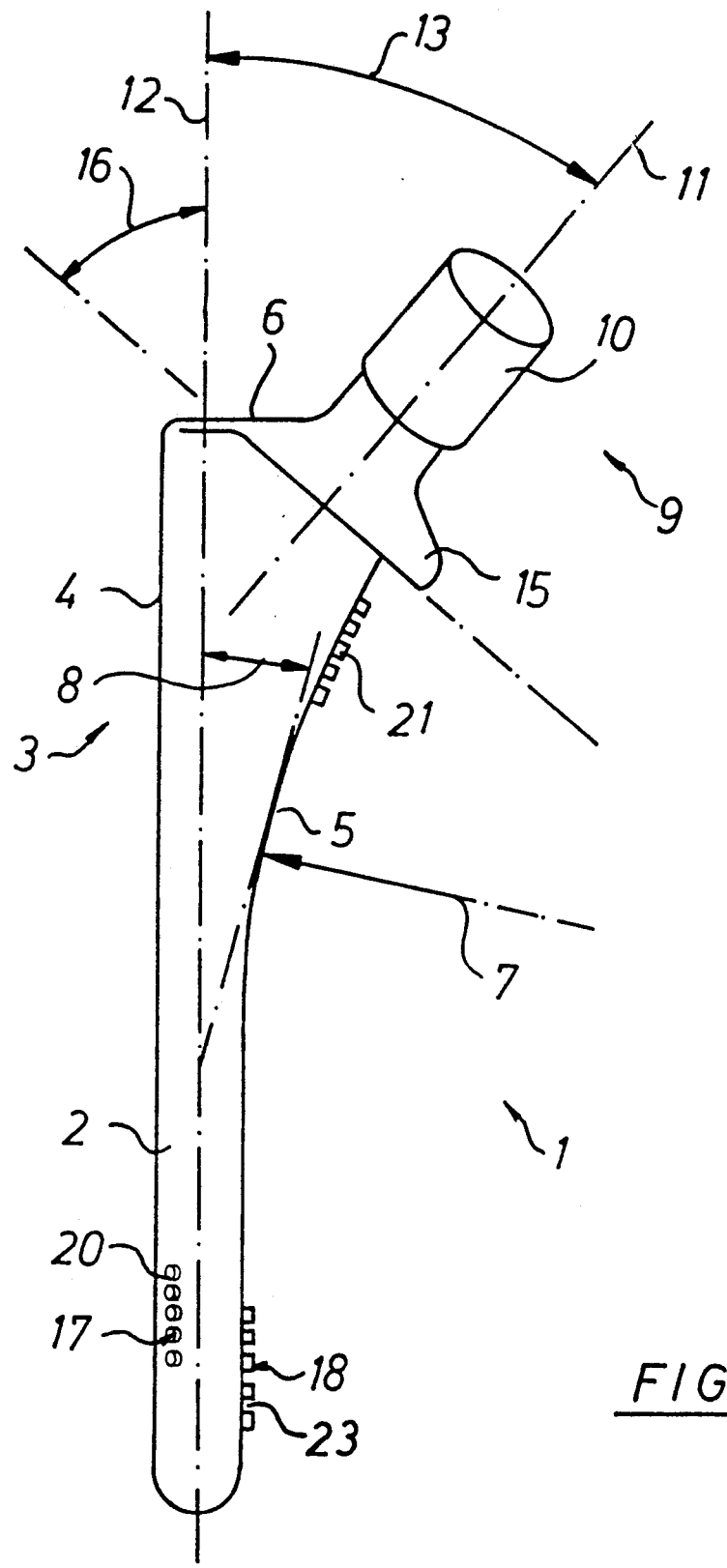
FIG. 1 is a side elevation of a femoral head shaft prosthesis according to the invention.

Referring now in more detail to the drawings, FIG. 1 shows a femoral head shaft prosthesis 1 consisting of a lower, cylindrical shaft portion 2 and an upper shaft portion 3. The upper shaft portion 3 is formed by a triangle-like structure which is defined by a vertical leg 4 which is a straight extension of the lower shaft portion 2, by a conical leg 5 curving out concavely and by a horizontal upper border 6. The triangular structure is of approximately the thickness of the cylindrical lower shaft portion 2.

Typical dimensions are a length of approximately 150 mm for the lower shaft portion 2 and the upper shaft portion, a cylindrical diameter of 2 to 12 mm for the lower shaft portion, a radius 7 of 135 mm for the concave curve and a tangential angle of inclination 8 of 15°. The shaft length and the diameter of the cylindrical lower shaft portion are available according to the individual dimensions of the individual receiving the implant.

A femoral head 9 consists of a cone 10, the cone axis 11 of which forms an angle 13 of 40° with the longitudinal axis 12 of the prothesis shaft. The cone 10 or the cone axis 11 is inclined forward by an angle 14 of 10° from the longitudinal axis 12 or the triangular surface (see FIG. 2). A collar 15 is attached under cone 10 and projects laterally beyond the area of the shaft while being inclined at an angle 16 of 50° from the longitudinal axis 12.

Lower shaft portion 2 preferably consist of an upper area and a lower area. The upper area is free of ridges or spacers and has a substantially uniform diameter. In the lower area of the lower shaft portion 2 three longitudinal raised areas on ridges in form of nub rows 17, 18, 19 are formed about the circumference. Each of the nub rows 17, 18, 19 is made up of five nubs 20 aligned in the longitudinal direction and are spaced at intervals 23. The nub rows 17, 18, 19 are offset against each other in height. An additional identical nub row 21 is attached on the concave arc 5 of the upper shaft portion 3. The nub rows 17, 18, 19 and 21 are approximately 15 Mm long, the nubs 20 are approximately 2.5 high and wide and the interval 23 is approximately equal to the width of a nub.

The marrow cavity of the femoral bone is drilled into a cylindrical shape to accept the lower shaft portion 2 for implantation, and for this known tools such as drills and mortisers are available. The upper area of the femoral bone is accordingly hollowed out to accept the upper shaft portion 3. The size of the seating cavity corresponds to the circumference which is defined by the outside of the nub rows 17, 18, 19 and 21.

The femoral head shaft prosthesis 1 is inserted into the receiving cavity thus treated and prepared with cement, whereby a cement layer 22 of uniform thickness of approximately 2.5 mm develops in the gap formed between the shaft portion 2, 3 and the inner surface of the marrow cavity and defined by the height of the nub rows 17, 18, 19 and 21 (see cross-section of FIG. 3). Excess cement is pressed out to the top during insertion. The uniform cement layer thickness or gap width is achieved thanks to only a few spacers in form of nubs 20 which have small surfaces and are at a distance from each other. Three offset spacers in form of nub rows 17, 18, 19 in the lower area of the circumference of the cylindrical lower shaft portion 2 are sufficient for centering in the cylindrically prepared receiving cavity. Further centering and spacing in the upper area of the receiving cavity is achieved by the nub row 21 which presses against the corticalis medial of the femoral neck stump. In order to compensate for possible diameter tolerances after the cylindrical preparation of the receiving cavity and to ensure secure centering with respect to the central cylinder axis, nub rows 17, 18, 19 with a certain overall shorter longitudinal extension are used. The cement layer is interrupted only minimally due to the fact that they are offset longitudinally along the shaft with respect to each other and due to the intervals 23 between the nubs 20.

The inserted shaft surface is furthermore roughed up with a preferred pore depth of 0.2 to 0.6 mm. The cylindrical receiving cavity is also provided on its inside with grooves in form of helicoidal or longitudinal grooves in order to achieve improved cement bonding between receiving cavity or marrow cavity and shaft surface. The uniform cement layer thickness of approx. 2.5 mm, the few interruptions of the cement layer at only a few locations and the improved cement bonding through the rough surfaces result in greater primary and long-term stability.

While a preferred embodiment of the invention has been described using specific terms, such description is for illustrative purposes only, and it is to be understood that changes and variations may be made without departing from the spirit or scope of the following claims.

What is claimed is:

1. A femoral head shaft prosthesis which includes a longitudinal shaft portion having a length for implantation in a marrow cavity of a femoral neck stump and secured by means of a cement layer surrounding the shaft portion, a femoral head portion integral with said shaft portion projecting laterally in relation to a longitudinal axis of the shaft portion, and said shaft having a generally smooth outer surface with a plurality of discrete raised areas having small surface areas relative to a circumference of said shaft portion raised areas comprising:

a plurality of circumferentially spaced lower spacers connected directly with said outer surface and projecting outwardly from a lower portion of said shaft portion for spacing and centering said shaft portion in a receiving cavity formed in said marrow cavity of the femoral neck stump;

said lower shaft portion and said lower spacers having a total outer diameter generally equal to an inner diameter of said receiving cavity;

an upper shaft portion formed on one side as a straight projection of said lower shaft portion having a medial side which widens conically to define a concave surface in a medial area of said upper shaft portion;

a plurality of upper spacers connecting directly with said outer surface and projecting outwardly from aid concave surface for contact against a corticalis medial in said marrow cavity; and said lower spacers providing a uniform gap for uniform cement layer thickness about said lower shaft with only minimal interruptions between said receiving cavity and shaft portion to ensure primary and long-term stability.

2. The prosthesis of claim 1 wherein said lower spacers includes rows of narrow nubs extending longitudinally along said shaft portion said nubs are relatively short compared to the shaft length, and are arranged to intervals between adjacent nubs.

3. The prosthesis of claim 2 including at least three of said nub rows distributed about a circumference of said lower shaft portion.

4. The prosthesis of claim 2 wherein said nub rows are offset relative to each other longitudinally along said shaft portion to minimize circumferential interruption of said cement layer.

5. The prosthesis of claim 1 wherein said spacers extend outwardly from said shaft to a height within a range between a required minimum thickness of a cement layer of approximately 1.5 mm and 3.5 mm.

6. The prosthesis of claim 1 wherein said spacers extend outwardly from said shaft to a height of about 2.5 mm.

7. The prosthesis of claim 1 wherein a surface of said shaft portion is roughened and has a preferred pore depth of about 0.2 to 0.6 mm.

8. The prosthesis of claim 1 wherein said medial side widens with a concave surface having a tangential angle of inclination (8) of about 15° relative to a longitudinal axis (12) of said shaft portion to define an approximately triangular surface having a thickness generally equal to a diameter of said lower shaft portion, said triangular surface being limited by a vertical limit, a horizontal limit, and said concave surface so that said femoral head is preferably in a form with a cone axis (10) at a 40° angle inclination relative to said longitudinal axis and terminates near an intersection of said horizontal limit and said concave surface.

9. The prosthesis of claim 8, including a collar, preferably having an inclination (16) of about 50 degrees in relation to said longitudinal axis (12) is provided below said femoral head adapted to be applied against the femoral neck.

10. A femoral head shaft prosthesis which includes a longitudinal lower shaft portion an intermediate shaft portion and an upper shaft portion for implantation in a marrow cavity of a femoral neck stump and being secured by a cement layer surrounding the shaft portion in said marrow cavity comprising:
   a femoral head portion integral with said upper shaft portion projecting laterally in relation to a longitudinal axis of the lower and intermediate shaft portions and shad shaft having a generally smooth outer surface with a plurality of discrete raised areas having small surface areas relative to a circumference of said shaft portion; said raised areas comprising:
   a plurality of lower spacers integral with said outer surfaces and projecting outwardly from said lower shaft portion for spacing and centering said shaft portion in a receiving cavity formed in said marrow cavity of the femoral neck stump, said intermediate shaft portion being free of spacers;
   said lower shaft portion and said lower spacers having a total outer diameter generally equal to an inner diameter of said receiving cavity;
   said intermediate shaft portion having an outer diameter substantially less than said diameter of said receiving cavity; and
   said lower spacers providing a uniform gap for uniform cement layer thickness with only minimal interruptions between said receiving cavity and shaft portion to ensure primary and long-term stability.

11. The prosthesis of claim 10 wherein said lower spacers includes rows of narrow nubs extending longitudinally along said lower shaft portion, said nubs rows being relatively short compared to the shaft length, and including spaces defined between adjacent nubs of said longitudinal rows for occupation of cement.

12. The prosthesis of claim 11 including at least three said nub rows distributed about a circumference of said lower shaft portion.

13. The prosthesis of claim 12 including:
   said femoral head portion being formed on one side as a straight projection of said shaft portion having a medial side which widens conically to define a concave surface in a medial area of an upper part of said shaft portion;
   a plurality of upper spacers projecting from said concave surface for contact against corticalis medial when said shaft portion is implanted in said marrow cavity.

14. The prosthesis of claim 13 wherein said medial side widens with a concave surface having a tangential angle of inclination of about 15° relative to a longitudinal axis of said shaft portion to define an approximately triangular surface having a thickness generally equal to a diameter of said lower and intermediate shaft portions, said triangular surface being limited by a vertical limit, a horizontal limit, and said concave surface so that said femoral head is preferably in a form with a cone axis at a 40° angle inclination relative to said longitudinal axis and terminates near an intersection of said horizontal limit and said concave surface.

15. The prosthesis of claim 14 including a collar, preferably having an inclination of about 50° in relation to said longitudinal axis said collar is provided below said femoral head and is adapted to be applied against the femoral neck.

16. The prosthesis of claim 12 wherein said nub rows are longitudinally offset relative to each other along said lower shaft portion to minimize circumferential interruption of said cement layer.

17. The prosthesis of claim 16 wherein said nubs extend outwardly from said shaft to a height within a range between a required minimum thickness of a cement layer of approximately 1.5 mm and 3.5 mm.

18. The prosthesis of claim 17 wherein a surface of said shaft portion is roughened and has a preferred pore depth of about 0.2 to 0.6 mm.

* * * * *